US012688934B2

(12) United States Patent
Kamai

(10) Patent No.: US 12,688,934 B2
(45) Date of Patent: Jul. 21, 2026

(54) WASTE IDENTIFICATION METHOD, WASTE IDENTIFICATION DEVICE, AND WASTE IDENTIFICATION PROGRAM

(71) Applicant: PANASONIC HOLDINGS CORPORATION, Osaka (JP)

(72) Inventor: Takahiro Kamai, Kyoto (JP)

(73) Assignee: PANASONIC HOUSING SOLUTIONS CO., LTD., Osaka (JP)

( * ) Notice: Subject to any disclaimer, the term of this patent is extended or adjusted under 35 U.S.C. 154(b) by 878 days.

(21) Appl. No.: 17/948,660

(22) Filed: Sep. 20, 2022

(65) Prior Publication Data

US 2023/0020686 A1 Jan. 19, 2023

Related U.S. Application Data

(63) Continuation of application No. PCT/JP2020/048939, filed on Dec. 25, 2020.

(60) Provisional application No. 62/993,910, filed on Mar. 24, 2020.

(30) Foreign Application Priority Data

Nov. 12, 2020 (JP) ................................. 2020-188527

(51) Int. Cl.
*G16H 40/67* (2018.01)
*A61B 7/00* (2006.01)
(52) U.S. Cl.
CPC ............. *G16H 40/67* (2018.01); *A61B 7/008* (2013.01)
(58) Field of Classification Search
CPC .................................. G16H 40/67; A61B 7/008
See application file for complete search history.

(56) References Cited

U.S. PATENT DOCUMENTS

| 11,540,760 B1* | 1/2023 | Guillemette ......... A47K 13/105 |
| 2016/0113618 A1* | 4/2016 | Su .......................... A61B 7/003 |
| | | 600/586 |
| 2018/0303466 A1* | 10/2018 | Kashyap ............ A61B 10/0038 |

(Continued)

FOREIGN PATENT DOCUMENTS

| JP | 07-216963 | 8/1995 |
| JP | 2009-258078 | 11/2009 |

(Continued)

OTHER PUBLICATIONS

International Search Report issued in International Pat. Appl. No. PCT/JP2020/048939, dated Mar. 9, 2021, along with an English translation thereof.

*Primary Examiner* — Fan S Tsang
*Assistant Examiner* — Tyler Michael Liebgott
(74) *Attorney, Agent, or Firm* — GREENBLUM & BERNSTEIN, P.L.C.

(57) ABSTRACT

An excreta identification device includes: a sound data acquisition unit that acquires sound data collected by a microphone arranged in a toilet; an excreta identification unit that identifies which of defecation, urination, and flatulating has been performed by inputting the acquired sound data to an identification model subjected to machine learning where sound data indicating any of defecation sound, urination sound, and flatulating sound is an input value, and which of defecation, urination, and flatulating has been performed is an output value; and an identification result output unit that outputs an identification result.

7 Claims, 8 Drawing Sheets

(56) References Cited

U.S. PATENT DOCUMENTS

2019/0008457 A1* 1/2019 Hall ..................... A61B 5/6891
2020/0297310 A1* 9/2020 Hall ........................ A61B 8/54

FOREIGN PATENT DOCUMENTS

JP          2015-178764          10/2015
JP          2020-012348           1/2020

* cited by examiner

FIG.3

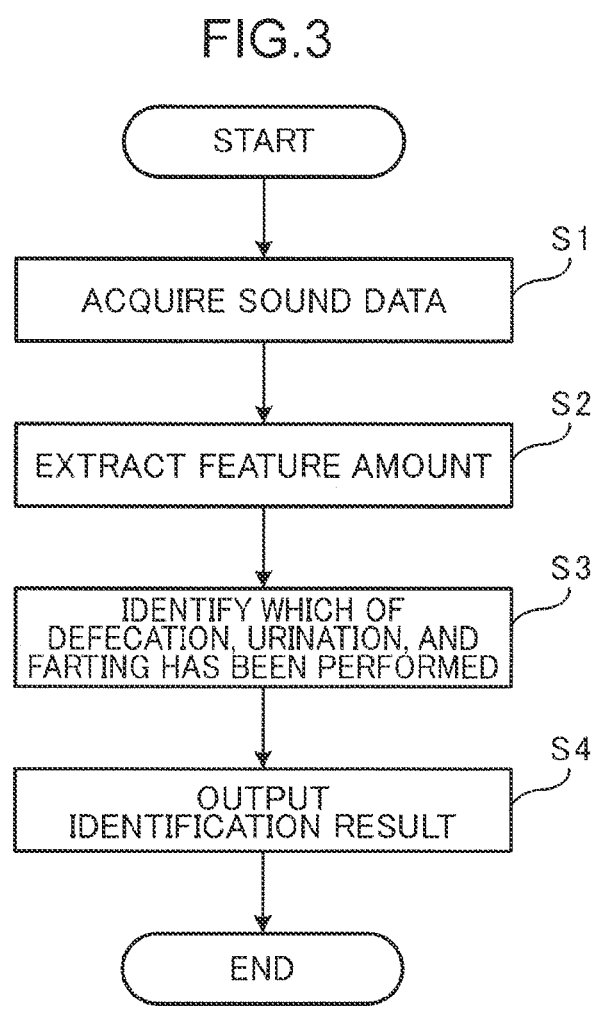

START

S1

ACQUIRE SOUND DATA

S2

EXTRACT FEATURE AMOUNT

S3

IDENTIFY WHICH OF
DEFECATION, URINATION, AND
FARTING HAS BEEN PERFORMED

S4

OUTPUT
IDENTIFICATION RESULT

END

FIG.4

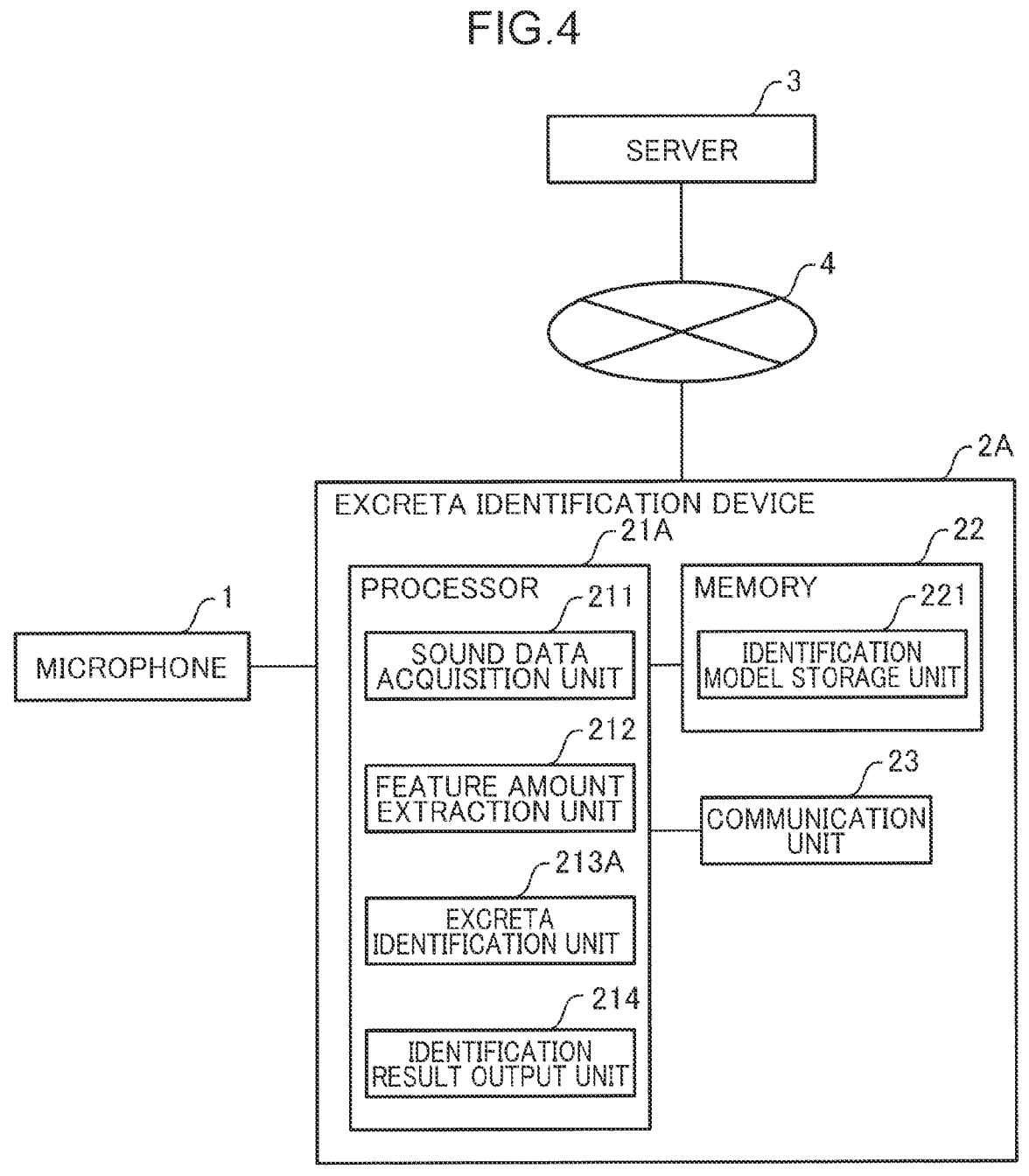

SERVER — 3

— 4

EXCRETA IDENTIFICATION DEVICE — 2A

MICROPHONE — 1

PROCESSOR — 21A

SOUND DATA ACQUISITION UNIT — 211

FEATURE AMOUNT EXTRACTION UNIT — 212

EXCRETA IDENTIFICATION UNIT — 213A

IDENTIFICATION RESULT OUTPUT UNIT — 214

MEMORY — 22

IDENTIFICATION MODEL STORAGE UNIT — 221

COMMUNICATION UNIT — 23

FIG.6

| CORRECT ANSWER SOUND | IDENTIFICATION RESULT | | | | | | | |
|---|---|---|---|---|---|---|---|---|
| | RUSTLING SOUND | DEFECATION SOUND | FARTING SOUND | COLLISION SOUND | NOZZLE OPERATING SOUND AND NOZZLE CLEANING SOUND | SILENCE | WATER DROPLET SOUND | URINATION SOUND |
| RUSTLING SOUND | 0.74 | 0.03 | 0.01 | 0.08 | 0.00 | 0.03 | 0.07 | 0.03 |
| DEFECATION SOUND | 0.02 | 0.78 | 0.01 | 0.00 | 0.00 | 0.00 | 0.09 | 0.09 |
| FARTING SOUND | 0.00 | 0.00 | 0.81 | 0.02 | 0.05 | 0.00 | 0.08 | 0.03 |
| COLLISION SOUND | 0.11 | 0.00 | 0.01 | 0.74 | 0.00 | 0.00 | 0.13 | 0.00 |
| NOZZLE OPERATING SOUND AND NOZZLE CLEANING SOUND | 0.06 | 0.00 | 0.15 | 0.01 | 0.44 | 0.01 | 0.02 | 0.32 |
| SILENCE | 0.01 | 0.01 | 0.02 | 0.09 | 0.01 | 0.46 | 0.40 | 0.01 |
| WATER DROPLET SOUND | 0.02 | 0.01 | 0.06 | 0.03 | 0.03 | 0.02 | 0.75 | 0.08 |
| URINATION SOUND | 0.00 | 0.00 | 0.07 | 0.00 | 0.00 | 0.03 | 0.25 | 0.65 |

WASTE IDENTIFICATION METHOD, WASTE IDENTIFICATION DEVICE, AND WASTE IDENTIFICATION PROGRAM

TECHNICAL FIELD

The present disclosure relates to a technique for identifying which of defecation, urination, and flatulating has been performed.

BACKGROUND ART

The presence or absence of excreta such as feces, urine, and flatulence, the type of excreta, the number of times of excreting, and the time of excreting are important information for managing the health of the care receiver. The caregiver records information on excreta of the care receiver, but the recording of the information is a burden on the caregiver and the care receiver. In addition, when recording information regarding excreta by a report from a care receiver, it is difficult to obtain accurate information regarding excreta from a care receiver with dementia.

Therefore, conventionally, an excretion management system that objectively manages excretion has been desired. For example, the excretion management system of Patent Literature 1 includes a temperature measurement part for measuring the space distribution of the temperature in a bowl part of a toilet bowl in noncontact and a control part that determines the presence or absence in the bowl part based on the temperature data. In addition, the conventional excretion management system further includes an odor measurement part for measuring an odor in the bowl part. Based on the odor data measured by an odor measurement part and the temperature data, the control part discriminates at least one of feces, urine, and flatulence as the excreta is excreted in the bowl part.

For example, the toilet seat device of Patent Literature 2 includes an underwater microphone, a determination reference sound storage unit, and a determination unit. The underwater microphone is provided underwater in order to prevent noise generated in the toilet from being picked up, and more selectively detects sound when there is a falling object underwater. The determination reference sound storage unit stores frequency characteristics and duration characteristics that are characteristic of sounds generated when feces in a diarrhea state, a constipation state, and a normal state fall into water. The determination unit compares the characteristics of an input signal with a feces state determination reference value in the determination reference sound storage unit. At this time, the determination unit determines the type of sound as to whether or not to be a sound when feces fall, and determines which of a diarrhea state, a constipation state, or a normal state the feces are in.

However, in the above-described conventional technique, it is difficult to accurately identify which of defecation, urination, and flatulating the one who excreted has performed, and further improvement has been required.

CITATION LIST

Patent Literature

Patent Literature 1: Japanese Patent Application Laid-Open No. 2015-178764
Patent Literature 2: Japanese Patent Application Laid-Open No. H7-216963

SUMMARY OF INVENTION

The present disclosure has been made to solve the above problems, and an object of the present disclosure is to provide a technique capable of accurately identifying which of defecation, urination, and flatulating the one who excreted has performed.

In an excreta identification method according to an aspect of the present disclosure, a computer acquires sound data collected by a microphone arranged in a toilet, identifies which of defecation, urination, and flatulating has been performed by inputting the acquired sound data to an identification model that has been subjected to machine learning where sound data indicating any of a defecation sound, a urination sound, and a flatulating sound is an input value, and which of defecation, urination, and flatulating has been performed is an output value, and outputs an identification result.

According to the present disclosure, it is possible to accurately identify which of defecation, urination, and flatulating the one who excreted has performed.

BRIEF DESCRIPTION OF DRAWINGS

FIG. 3 is a flowchart for describing excreta identification processing in the excreta identification device according to the first embodiment of the present disclosure.

FIG. 4 is a view illustrating a configuration of an excretion management system in a second embodiment of the present disclosure.

FIG. 6 is a view illustrating an example of a confusion matrix representing an identification result for a correct answer sound in the present second embodiment.

Figure 1:
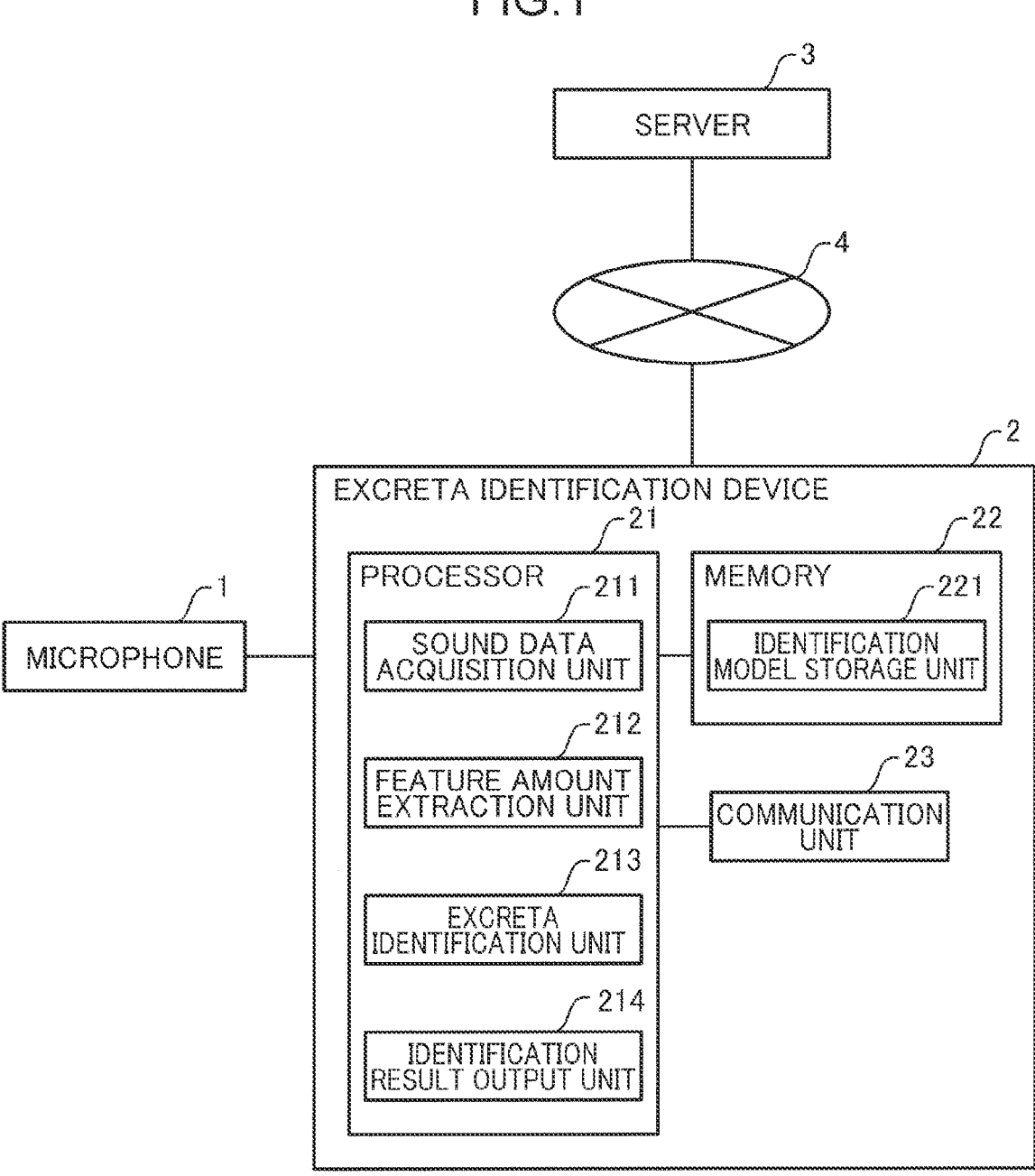
FIG. 1 is a view illustrating a configuration of an excretion management system in a first embodiment of the present disclosure.

DESCRIPTION OF EMBODIMENTS (Knowledge Underlying Present Disclosure)

In the excretion management system of Patent Literature 1, the control part compares the temperature data T ich at each time with the temperature threshold value $T_n$ for the temperature time series data, determines that excretion is not performed when $T_{i,ch} \leq T_n$, and determines that excretion is performed when $T_{i,ch} > T_n$.

The odor measurement part includes a hydrogen sulfide odor sensor having high sensitivity to a hydrogen sulfide odor and an ammonia odor sensor having high sensitivity to an ammonia odor. The control part compares the odor data $O_{1i}$ at each time in the odor time series data of the hydrogen sulfide odor sensor with the first odor threshold value $O_{n1}$, and compares the odor data $O_{2i}$ at each time in the odor time series data of the ammonia odor sensor with the second odor threshold value $O_{n2}$. When the temperature data $T_{i,ch}$ at each time of the temperature time series data is $T_{i,ch} > T_n$, that is, when excretion is performed, the control part determines that the excretion is feces if $O_{1i} > O_{n1}$ or $O_{2i} > O_{n2}$, and determines that the excretion is urine if $O_{1i} \leq O_{n1}$ and $O_{2i} \leq O_{n2}$. In addition, when the temperature data $T_{i,ch}$ at each time of the temperature time series data is $T_{i,ch} \leq T_n$, that is, when excretion is not performed, the control part determines that flatulence has occurred if $O_{1i} > O_{n1}$ or $O_{2i} > O_{n2}$.

As described above, based on temperature data, odor data of the hydrogen sulfide odor sensor, and odor data of the ammonia odor sensor, the conventional technique discriminates as to which of feces, urine, or flatulence is the excreta.

However, when excretion is performed with the toilet bowl in a high-temperature area, there is a possibility that temperature of the excreta falling in the bowl part becomes lower than the temperature in the bowl part before excretion, and it is difficult to accurately determine whether or not excretion has been performed.

In addition, the concentration of the hydrogen sulfide component contained in the gas excreted from the anus of one who excreted changes depending on the physical condition such as constipation of the one who excreted. In addition, the concentration of the hydrogen sulfide component contained in the excreted gas greatly changes depending on the food eaten by the one who excreted, and also greatly changes depending on the medicine taken.

Therefore, it is difficult to accurately determine which of defecation, urination, and flatulating the one who excreted has performed using the concentration of the hydrogen sulfide component contained in the excreta.

The toilet seat device of Patent Literature 2 detects, with the microphone provided underwater, the sound of feces falling into water, and determines which of a diarrhea state, a constipation state, or a normal state the feces are in, but does not determine which of feces, urine, and flatulence is the excreta is. In addition, in Patent Literature 2, since the microphone is provided underwater, it is difficult to detect a urination sound and a flatulating sound with high accuracy.

In order to solve the above problem, in an excreta identification method according to an aspect of the present disclosure, a computer acquires sound data collected by a microphone arranged in a toilet, identifies which of defecation, urination, and flatulating has been performed by inputting the acquired sound data to an identification model that has been subjected to machine learning where sound data indicating any of defecation sound, urination sound, and flatulating sound is an input value, and which of defecation, urination, and flatulating has been performed is an output value, and outputs an identification result.

According to this configuration, the identification model is subjected to machine learning, where sound data indicating any of defecation sound, urination sound, and flatulating sound is an input value, and which of defecation, urination, and flatulating has been performed is an output value. By inputting, into the identification model, the sound data collected by the microphone arranged in the toilet, which of defecation, urination, and flatulating has been performed is identified, and therefore it is possible to accurately identify which of defecation, urination, and flatulating the one who excreted has performed.

In the excreta identification method, the identification model may be subjected to machine learning where sound data indicating any of defecation sound, urination sound, flatulating sound, and an environmental sound generated in the toilet is an input value, and which of defecation, urination, and flatulating has been performed or a generation situation of the environmental sound is an output value, and in the identification, which of defecation, urination, and flatulating has been performed or the generation situation of the environmental sound may be identified by inputting the acquired sound data to the identification model.

In the toilet, various environmental sounds are generated other than defecation sound, urination sound, and flatulating sound. Therefore, by performing machine learning not only for defecation sound, urination sound, and flatulating sound but also for environmental sound generated in the toilet, it is possible to identify also the generation situation of the environmental sound in addition to which of defecation, urination, and flatulating has been performed. In addition, by identifying also the generation situation of the environmental sound, it is possible to improve the identification accuracy of defecation, urination, and flatulating.

In the excreta identification method, the identification model may be subjected to machine learning where sound data indicating each of a plurality of levels of urination sound divided according to urine stream is an input value, and which level of urination sound among the plurality of levels of urination sound urination corresponding to has been performed is an output value, in the identification, by inputting the acquired sound data to the identification model, it may be identified as to which level of urination sound among a plurality of levels of urination sound urination corresponding to has been performed, time at which it is continuously identified that the urination has been performed may be measured, and a voided volume may be calculated using the identified level of urination and the measured time.

The urination sound changes in accordance with the urine stream. By identifying the level of the urine stream, it is possible to estimate the amount of urine excreted per predetermined time (for example, one second). Therefore, it is possible to estimate the voided volume using the identified level of urination and the measured time of continued urination.

In the above-described excreta identification method, the identification model may be subjected to machine learning where sound data indicating defecation sound according to a state of feces is an input value, and a state of feces is an output value, and in the identification, a state of feces may be identified by inputting the acquired sound data to the identification model.

The defecation sound changes in accordance with the state of feces. That is, defecation sound when hard feces is excreted is different from defecation sound when watery feces is excreted. Therefore, by performing machine learning also for defecation sound according to the state of feces, it is possible to identify also the state of feces in addition to which of defecation, urination, and flatulating has been performed. In addition, by identifying the state of feces, it is possible to manage in more detail the physical condition of the one who excreted.

In the excreta identification method, the identification model may be subjected to machine learning where sound data indicating sound of water splashed on the microphone is an input value, and that water is splashed on the microphone is an output value, and in the identification, it may be identified that water is splashed on the microphone by inputting the acquired sound data to the identification model.

When water is splashed on the microphone, there is concern that the performance of the microphone is deteriorated. Then, it is possible to identify that water is splashed on the microphone by performing machine learning on the sound of water splashed on the microphone. This makes it possible to prompt cleaning or maintenance of the microphone, maintain performance of the microphone, and prevent deterioration of the microphone.

Furthermore, in the above-described excreta identification method, in acquisition of the sound data, the sound data from when one who excreted sits on a toilet seat to when he/she leaves the toilet seat may be acquired.

According to this configuration, since the sound data from when one who excreted sits on a toilet seat to when he/she leaves the toilet seat is acquired, as compared with continuously acquiring the sound data at all times, the load of identification processing can be reduced and the capacity of the memory for storing the sound data can be reduced.

In the excreta identification method, the microphone may be arranged inside a toilet bowl.

According to this configuration, since the microphone is arranged inside the toilet bowl, it is possible to acquire, with higher accuracy, defecation sound, urination sound, and flatulating sound generated in the toilet bowl.

An excreta identification device according to another aspect of the present disclosure includes: an acquisition unit that acquires sound data collected by a microphone arranged in a toilet; an identification unit that identifies which of defecation, urination, and flatulating has been performed by inputting the acquired sound data to an identification model that has been subjected to machine learning where sound data indicating any of defecation sound, urination sound, and flatulating sound is an input value, and which of defecation, urination, and flatulating has been performed is an output value; and an output unit that outputs an identification result.

According to this configuration, the identification model is subjected to machine learning, where sound data indicating any of defecation sound, urination sound, and flatulating sound is an input value, and which of defecation, urination, and flatulating has been performed is an output value. By inputting, into the identification model, the sound data collected by the microphone arranged in the toilet, which of defecation, urination, and flatulating has been performed is identified, and therefore it is possible to accurately identify which of defecation, urination, and flatulating the one who excreted has performed.

A non-transitory computer readable recording medium storing an excreta identification program according to another aspect of the present disclosure causes a computer to function to acquire sound data collected by a microphone arranged in a toilet, identify which of defecation, urination, and flatulating has been performed by inputting the acquired sound data to an identification model that has been subjected to machine learning where sound data indicating any of defecation sound, urination sound, and flatulating sound is an input value, and which of defecation, urination, and flatulating has been performed is an output value, and output an identification result.

According to this configuration, the identification model is subjected to machine learning, where sound data indicating any of defecation sound, urination sound, and flatulating sound is an input value, and which of defecation, urination, and flatulating has been performed is an output value. By inputting, into the identification model, the sound data collected by the microphone arranged in the toilet, which of defecation, urination, and flatulating has been performed is identified, and therefore it is possible to accurately identify which of defecation, urination, and flatulating the one who excreted has performed.

Embodiments of the present disclosure will be described below with reference to the accompanying drawings. The following embodiments are examples of embodiment of the present disclosure, and are not intended to limit the technical scope of the present disclosure.

First Embodiment

Figure 2:
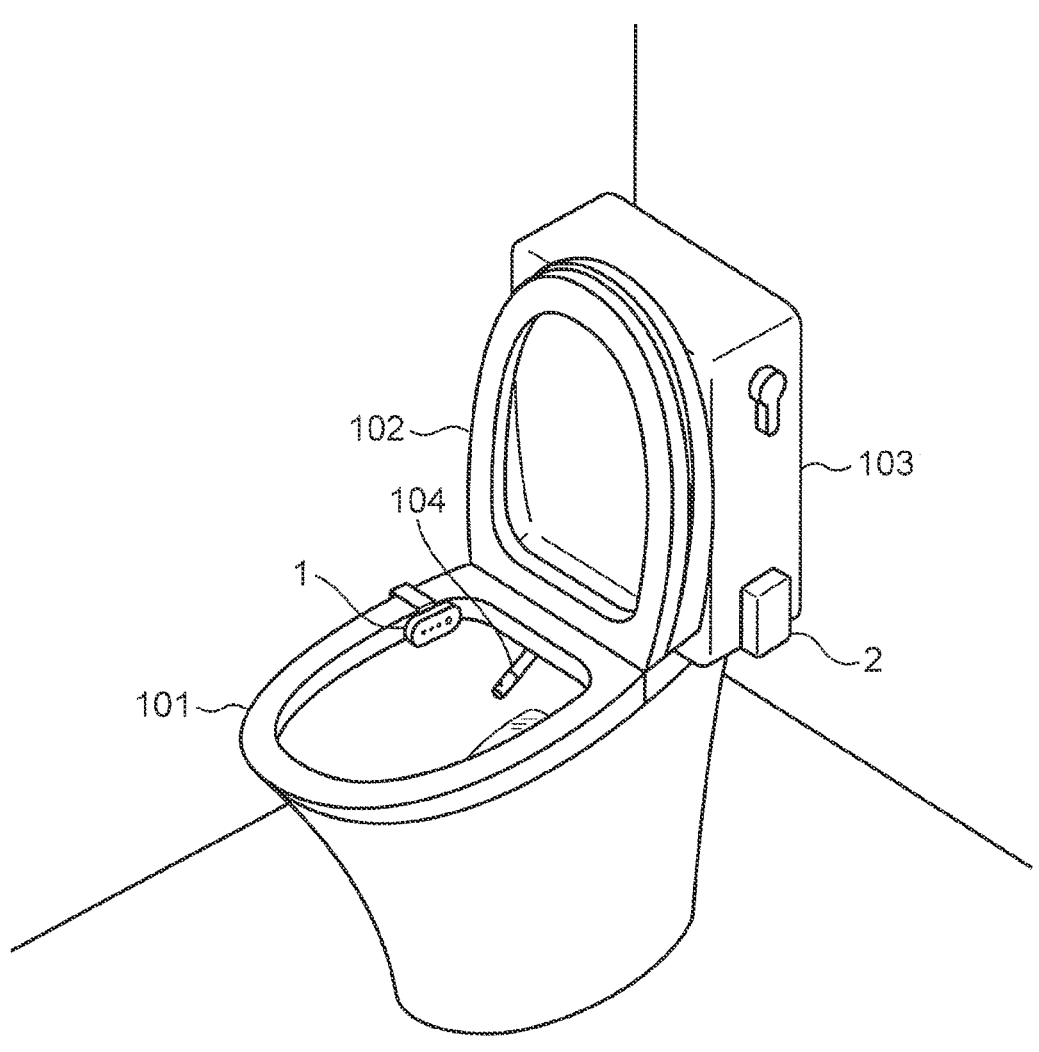
FIG. 2 is a view for describing arrangement positions of a microphone and an excreta identification device in the first embodiment of the present disclosure.

FIG. 1 is a view illustrating the configuration of an excretion management system in the first embodiment of the present disclosure. FIG. 2 is a view for describing the arrangement positions of a microphone 1 and an excreta identification device 2 in the first embodiment of the present disclosure.

The excretion management system illustrated in FIG. 1 includes a microphone 1, an excreta identification device 2, and a server 3.

The microphone 1 is arranged in a toilet. As illustrated in FIG. 2, the microphone 1 is bung on an edge of an opening formed in an upper part of the toilet bowl 101 that receives feces and urine. The microphone 1 is arranged inside the toilet bowl 101 and collects sound in the toilet bowl 101. The microphone 1 is connected to the excreta identification device 2 communicably with each other in a wired or wireless manner. The microphone 1 transmits the collected sound data to the excreta identification device 2.

The microphone 1 is, for example, a micro electro mechanical systems (MEMS) microphone. Since the MEMS microphone can be downsized and is resistant to water, it is optimal as a microphone arranged inside the toilet bowl 101.

A bottom part of the toilet bowl 101 is provided with a drain channel not illustrated. Feces and urine excreted into the toilet bowl 101 are caused to flow through the drain channel. An upper part of the toilet bowl 101 is provided with a toilet seat 102 for the one who excreted to sit. The toilet seat 102 rotates up and down. The one who excreted sits down in a state where the toilet seat 102 is lowered onto the toilet bowl 101. A rear of the toilet bowl 101 is provided with a flush tank 103 that stores water for flushing feces and urine.

The toilet bowl 101 is provided with a shower nozzle 104. The shower nozzle 104 releases cleaning water upward to wash a pubic region of a person. A controller not illustrated instructs start and stop of a cleaning operation by the shower nozzle 104. The shower nozzle 104 has a function of cleaning a pubic region of a person and a function of cleaning the shower nozzle 104 itself. When the cleaning operation for a person is stopped, the shower nozzle 104 is automatically cleaned.

Note that the microphone 1 may constantly transmit the collected sound data to the excreta identification device 2. In addition, the microphone 1 may transmit, to the excreta identification device 2, sound data collected in a period from a time point at which the one who excreted sits on the toilet seat 102 to a time point at which the one who excreted leaves the toilet seat 102. For example, the toilet seat 102 may be provided with a pressure sensor, and whether or not the one who excreted sits on the toilet seat 102 may be determined based on output from the pressure sensor. Furthermore, determination as to whether the one who excreted sits on the toilet seat 102 may be made by using the fact that the inside of the toilet bowl 101 is darkened when the one who excreted sits on the toilet seat 102. That is, inside the toilet bowl 101 is provided with a light sensor, and when the light sensor detects that the toilet bowl is darkened, it may be determined that the one who excreted has sat on the toilet seat 102, and when the light sensor detects that the toilet bowl is brightened, it may be determined that the one who excreted left the toilet seat 102.

The excreta identification device 2 is arranged, for example, on a side surface of the flush tank 103. Note that the arrangement position of the excreta identification device 2 is not limited to the above, and may be any position as long as it is in the toilet. When the microphone 1 and the excreta identification device 2 are wirelessly connected to each other, the excreta identification device 2 needs not be arranged inside the toilet and only needs to be arranged at a place where wireless communication with the microphone 1 in the house is possible.

The excreta identification device 2 includes a processor 21, a memory 22, and a communication unit 23.

The memory 22 is a storage device capable of storing various types of information, such as a random access memory (RAM), a solid state drive (SSD), or a flash memory. The memory 22 stores the sound data transmitted by the microphone 1.

In addition, the memory 22 includes an identification model storage unit 221. The identification model storage unit 221 stores in advance an identification model that has been subjected to machine learning where sound data indicating any of defecation sound, urination sound, and flatulating sound is an input value, and which of defecation, urination, and flatulating has been performed is an output value.

As the machine learning, for example, supervised learning is used, where a relationship between an input and an output is learned using training data in which a label (output information) is given to input information. Note that as the machine learning, for example, unsupervised learning, where a structure of data is constructed only from an unlabeled input, semi-supervised learning, where both labeled and unlabeled are handled, reinforcement learning, where behavior that maximizes reward is learned by trial and error, and the like may be used. Furthermore, specific methods of machine learning include a neural network (including deep learning using a multilayer neural network), genetic programming, a decision tree, a Bayesian network, and a support vector machine (SVM). In the machine learning of the present disclosure, for example, a deep neural network (DNN) or a convolutional neural network (CNN) is used.

The processor 21 is, for example, a central processing unit (CPU). The processor 21 implements a sound data acquisition unit 211, a feature amount extraction unit 212, an excreta identification unit 213, and an identification result output unit 214.

The sound data acquisition unit 211 acquires sound data collected by the microphone 1 arranged inside the toilet. The sound data acquisition unit 211 acquires sound data from the memory 22. The sound data acquisition unit 211 reads sound data stored in the memory 22.

The feature amount extraction unit 212 extracts a feature amount from the sound data acquired by the sound data acquisition unit 211. The feature amount is, for example, a mel-frequency cepstrum coefficient (MFCC). Note that MFCC is an example of the feature amount. The feature amount extraction unit 212 may extract another feature amount such as a cepstrum.

The excreta identification unit 213 identifies which of defecation, urination, and flatulating has been performed by inputting the acquired sound data to an identification model that has been subjected to machine learning where sound data indicating any of defecation sound, urination sound, and flatulating sound is an input value, and which of defecation, urination, and flatulating has been performed is an output value. The excreta identification unit 213 reads an identification model from the identification model storage unit 221, inputs, to the identification model, the feature amount of sound data extracted by the feature amount extraction unit 212, and acquires, from the identification model, an identification result of identifying which of defecation, urination, and flatulating has been performed. For example, when a feature amount of sound data indicating defecation sound is input to the identification model, an identification result indicating that defecation has been performed is output from the identification model.

The identification result output unit 214 outputs an identification result of identifying which of defecation, urination, and flatulating has been performed. The identification result output unit 214 transmits, to the server 3 via the communication unit 23, identification result information indicating which of defecation, urination, and flatulating has been performed.

When it is identified that any of defecation, urination, and flatulating has been performed, the identification result output unit 214 may transmit, to the server 3 via the communication unit 23, identification result information indicating that any of defecation, urination, and flatulating has been performed and date and time information indicating the date and time when any of defecation, urination, and flatulating is performed. In a case where none of defecation, urination, and flatulating has been performed, the identification result output unit 214 may transmit, to the server 3, or needs not transmit, to the server 3, identification result information indicating that none of defecation, urination, and flatulating has been performed.

The communication unit 23 transmits, to the server 3, an identification result indicating which of defecation, urination, and flatulating has been performed. The excreta identification device 2 is communicably connected to the server 3 via a network 4. The network 4 is the Internet, for example.

The server 3 receives identification result information indicating that any of defecation, urination, and flatulating has been performed that is transmitted by the excreta identification device 2. The server 3 may receive identification result information indicating that any of defecation, urination, and flatulating has been performed, and date and time information indicating the date and time when any of defecation, urination, and flatulating is performed. The server 3 includes a database that stores identification information for identifying the room or the house in which the excreta identification device 2 is arranged, identification result information indicating that any of defecation, urination, and flatulating has been performed, and date and time information indicating the date and time when any of defecation, urination, and flatulating is performed in association with one another. The identification information may be identification information for identifying a resident (one who excreted) of the room or the house in which the excreta identification device 2 is arranged.

For example, the caregiver uses a database of the server 3 when creating monitoring data of the care receiver. That is, a terminal device used by the caregiver acquires, from the server 3, the identification result information and the date and time information corresponding to the identification information of the care receiver, and creates monitoring data of the care receiver. For example, the terminal device may create the number of times of defecation, urination, and flatulating in one day as the monitoring data, may create the number of times of defecation, urination, and flatulating in one week as the monitoring data, or may create the number of times of defecation, urination, and flatulating in one month as the monitoring data. Furthermore, for example, the terminal device may create the time of defecation, urination, and flatulating in one day as the monitoring data, may create the date and time of defecation, urination, and flatulating in one week as the monitoring data, or may create the date and time of defecation, urination, and flatulating in one month as the monitoring data.

Next, the excreta identification processing in the excreta identification device 2 according to the first embodiment of the present disclosure will be described.

FIG. 3 is a flowchart for describing the excreta identification processing in the exereta identification device 2 according to the first embodiment of the present disclosure.

First, in step S1, the sound data acquisition unit 211 acquires, from the memory 22, sound data collected inside the toilet bowl 101 by the microphone 1. For example, the exereta identification processing illustrated in FIG. 3 is performed once a day. The sound data acquisition unit 211 acquires the sound data for one day at 0:00 AM, for example. Note that the time at which the sound data is acquired is not limited to 0:00 AM. In addition, the excreta identification processing illustrated in FIG. 3 is not limited to be performed once a day, and may be performed a plurality of times a day, once a week, or every predetermined period.

In addition, the sound data acquisition unit 211 may acquire the sound data in the period from the time point at which the one who excreted sits on the toilet seat 102 to the time point at which the one who excreted leaves the toilet seat 102. In a case where excreta is excreted a plurality of times in one day, the sound data acquisition unit 211 may acquire a plurality of sound data for one day. Then, the excreta identification processing may be performed for each of the plurality of sound data.

Furthermore, the excreta identification processing illustrated in FIG. 3 may be performed in real time. That is, the sound data acquisition unit 211 may acquire the sound data in real time. The feature amount extraction unit 212 may divide the sound data into a plurality of frames and extract the feature amount for each frame. Therefore, the excreta identification processing may be performed every time sound data for one frame is acquired, or the excreta identification processing may be performed every time sound data for a plurality of frames is acquired.

Next, in step S2, the feature amount extraction unit 212 extracts a feature amount from the sound data acquired by the sound data acquisition unit 211.

Next, in step S3, the exereta identification unit 213 reads an identification model from the identification model storage unit 221, and inputs, to the read identification model, the feature amount extracted by the feature amount extraction unit 212, thereby identifying which of defecation, urination, and flatulating has been performed.

Next, in step S4, the identification result output unit 214 outputs an identification result as to which of defecation, urination, and flatulating has been performed. For example, the identification result output unit 214 transmits, to the server 3 via the communication unit 23, identification result information indicating which of defecation, urination, and flatulating has been performed, and date and time information indicating the date and time when any of defecation, urination, and flatulating is performed.

Note that the identification result output unit 214 may store, in the memory 22, identification result information indicating which of defecation, urination, and flatulating has been performed, and date and time information indicating the date and time when any of defecation, urination, and flatulating is performed. The memory 22 may include a universal serial bus (USB) memory connected to a USB port. The identification result output unit 214 may store, in a USB memory, identification result information indicating which of defecation, urination, and flatulating has been performed, and date and time information indicating the date and time when any of defecation, urination, and flatulating is performed.

As described above, the identification model is subjected to machine learning, where sound data indicating any of defecation sound, urination sound, and flatulating sound is an input value, and which of defecation, urination, and flatulating has been performed is an output value. By inputting, into the identification model, the sound data collected by the microphone 1 arranged in the toilet, which of defecation, urination, and flatulating has been performed is identified, and therefore it is possible to accurately identify which of defecation, urination, and flatulating the one who excreted has performed.

In addition, the identification model may be subjected to machine learning where sound data indicating defecation sound according to a state of feces is an input value, and a state of feces is an output value. Then, the excreta identification unit 213 may further identify the state of feces by inputting the acquired sound data to the identification model. Indices for classifying the state of feces incudes the Bristol stool scale. According to the Bristol stool scale, the state of feces is classified into separate hard lumps feces, lumpy feces, slightly lumpy feces, normal feces, slightly soft feces, mushy feces, and watery feces. By the identification model being subjected to machine learning where sound data indicating defecation sound according to a state of feces is an input value, and a state of feces is an output value, it becomes possible to identify not only whether or not to have defecated but also the state of the feces. The state of feces is not limited to the above seven types, and may be more than seven types or may be less than seven types.

In addition, the identification model may be subjected to machine learning where sound data indicating sound of water splashed on the microphone 1 is an input value, and that water is splashed on the microphone 1 is an output value. Then, the excreta identification unit 213 may further identify that water is splashed on the microphone 1 by inputting the acquired sound data to the identification model. When water is splashed on the microphone 1, there is concern that the performance of the microphone 1 is deteriorated. Then, the identification result output unit 214 may transmit, to the manager's terminal with, as an identification result, that water has been splashed on the microphone 1. This makes it possible to prompt cleaning or maintenance of the microphone 1, maintain performance of the microphone 1, and prevent deterioration of the microphone 1.

Second Embodiment

In the first embodiment, which of defecation, urination, and flatulating has been performed is identified. On the other hand, in the second embodiment, a generation situation of environmental sound is further identified in addition to which of defecation, urination, and flatulating has been performed.

FIG. 4 is a view illustrating the configuration of an excretion management system in the second embodiment of the present disclosure. The arrangement positions of the microphone 1 and the excreta identification device 2A in the second embodiment of the present disclosure are the same as the arrangement positions of the microphone 1 and the excreta identification device 2 in the first embodiment.

The excretion management system illustrated in FIG. 4 includes the microphone 1, an excreta identification device 2A, and the server 3. In the present second embodiment, the same components as those in the first embodiment are given the same reference numerals, and description will be omitted.

The excreta identification device 2A includes a processor 21A, the memory 22, and the communication unit 23.

The processor 21A is, for example, a CPU. The processor 21A implements the sound data acquisition unit 211, the feature amount extraction unit 212, an excreta identification unit 213A, and the identification result output unit 214.

The identification model is subjected to machine learning where sound data indicating any of defecation sound, urination sound, flatulating sound, and an environmental sound generated in the toilet is an input value, and which of defecation, urination, and flatulating has been performed or a generation situation of the environmental sound is an output value.

In the toilet, various environmental sounds are generated in addition to defecation sound, urination sound, and flatulating sound. Examples of the environmental sound include rustling sound, collision sound, nozzle operating sound, nozzle cleaning sound, water droplet sound, water flow sound, ventilation sound, and silence.

By inputting the acquired sound data to the identification model, the excreta identification unit 213A identifies which of defecation, urination, and flatulating has been performed or the generation situation of environmental sound. For example, the generation situation of the rustling sound is a situation of putting on or taking off a cloth. The generation situation of the collision sound is a situation in which objects collides with each other. The generation situation of the nozzle operating sound is a state where the shower nozzle 104 is cleaning a pubic region of a person. The generation situation of the nozzle cleaning sound is a state where the shower nozzle 104 cleaning itself. The generation situation of the water droplet sound is a situation where a water droplet falls from the shower nozzle 104. The generation situation of the water flow sound is a situation where feces or urine is flushed by the water. The generation situation of the ventilation sound is a situation where a ventilation fan is operating. In addition, silence is a situation in which no sound is generated.

Next, the excreta identification processing in the excreta identification device 2A according to the second embodiment of the present disclosure will be described.

Figure 5:
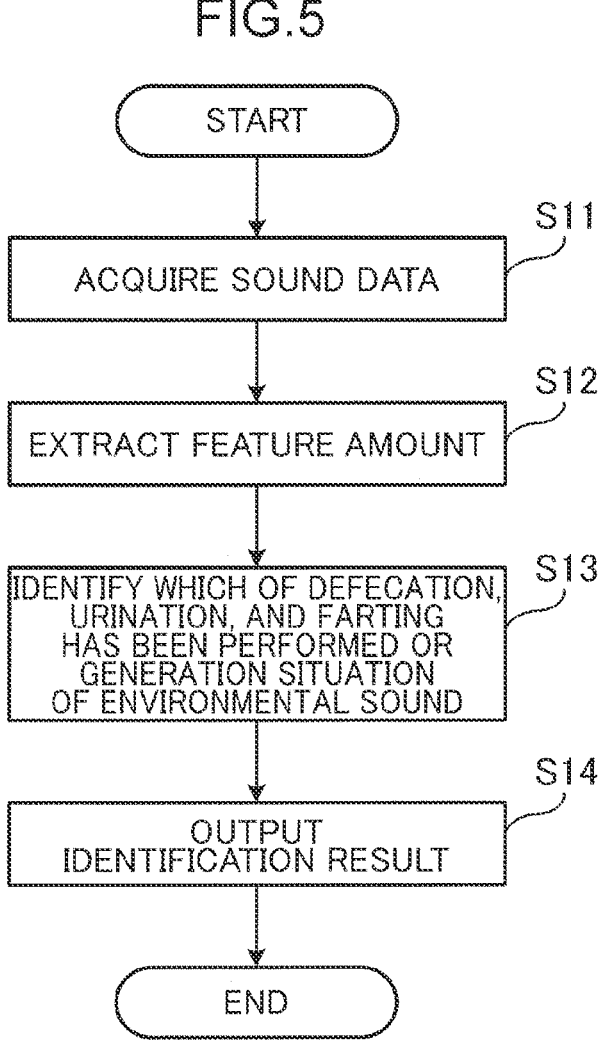
FIG. 5 is a flowchart for describing excreta identification processing in the excreta identification device according to the second embodiment of the present disclosure.

FIG. 5 is a flowchart for describing the excreta identification processing in the excreta identification device 2A according to the second embodiment of the present disclosure.

The processing in steps S11 and S12 is the same as the processing in steps S1 and S2 illustrated in FIG. 3, and thus description is omitted.

Next, in step S13, the excreta identification unit 213A reads an identification model from the identification model storage unit 221, and inputs, to the read identification model, the feature amount extracted by the feature amount extraction unit 212, thereby identifying which of defecation, urination, and flatulating has been performed or the generation situation of environmental sound.

Next, in step S14, the identification result output unit 214 outputs an identification result of which of defecation, urination, and flatulating has been performed or the generation situation of environmental sound. For example, the identification result output unit 214 transmits, to the server 3 via the communication unit 23, identification result information indicating which of defecation, urination, and flatulating has been performed or the generation situation of environmental sound, and date and time information indicating the date and time when any of defecation, urination, and flatulating is performed or the date and time when the environmental sound is generated.

Note that the identification result output unit 214 may store, in the memory 22, identification result information indicating which of defecation, urination, and flatulating has been performed or the generation situation of environmental sound, and date and time information indicating the date and time when any of defecation, urination, and flatulating is performed or the date and time when the environmental sound is generated. Furthermore, the memory 22 may include a USB memory connected to a USB port. The identification result output unit 214 may store, in a USB memory, identification result information indicating which of defecation, urination, and flatulating has been performed or the generation situation of environmental sound, and date and time information indicating the date and time when any of defecation, urination, and flatulating is performed or the date and time when the environmental sound is generated.

FIG. 6 is a view illustrating an example of a confusion matrix representing an identification result for a correct answer sound in the present second embodiment. In FIG. 6, the vertical axis direction indicates the correct answer sound, and the horizontal axis direction indicates the sound of the identification result.

For example, the ratio of correctly identifying the rustling sound as rustling sound is 0.74, and the ratio of incorrectly identifying the rustling sound as defecation sound is 0.03.

The ratio of correctly identifying the defecation as defecation sound was 0.78, the ratio of correctly identifying the flatulating sound as flatulating sound was 0.81, the ratio of correctly identifying the collision sound as collision sound was 0.74, the ratio of correctly identifying the nozzle operating sound and the nozzle cleaning sound as nozzle operating sound and the nozzle cleaning sound was 0.44, the ratio of correctly identifying the silence as silence was 0.46, the ratio of correctly identifying the water droplet sound as water droplet sound was 0.75, and the ratio of correctly identifying the urination sound as urination sound was 0.65.

As described above, for any identification result with respect to the correct answer sound, the ratio of correctly identifying is higher than the ration of incorrectly identifying.

As described above, in the toilet, various environmental sounds are generated other than defecation sound, urination sound, and flatulating sound. Therefore, by performing machine learning not only for defecation sound, urination sound, and flatulating sound but also for environmental sound generated in the toilet, it is possible to identify also the generation situation of the environmental sound in addition to which of defecation, urination, and flatulating has been performed. In addition, by identifying also the generation situation of the environmental sound, it is possible to improve the identification accuracy of defecation, urination, and flatulating.

Third Embodiment

In the first embodiment, which of defecation, urination, and flatulating has been performed is identified. On the other hand, in the third embodiment, which of defecation, urination, and flatulating has been performed is identified, and a voided volume is calculated.

Figure 7:
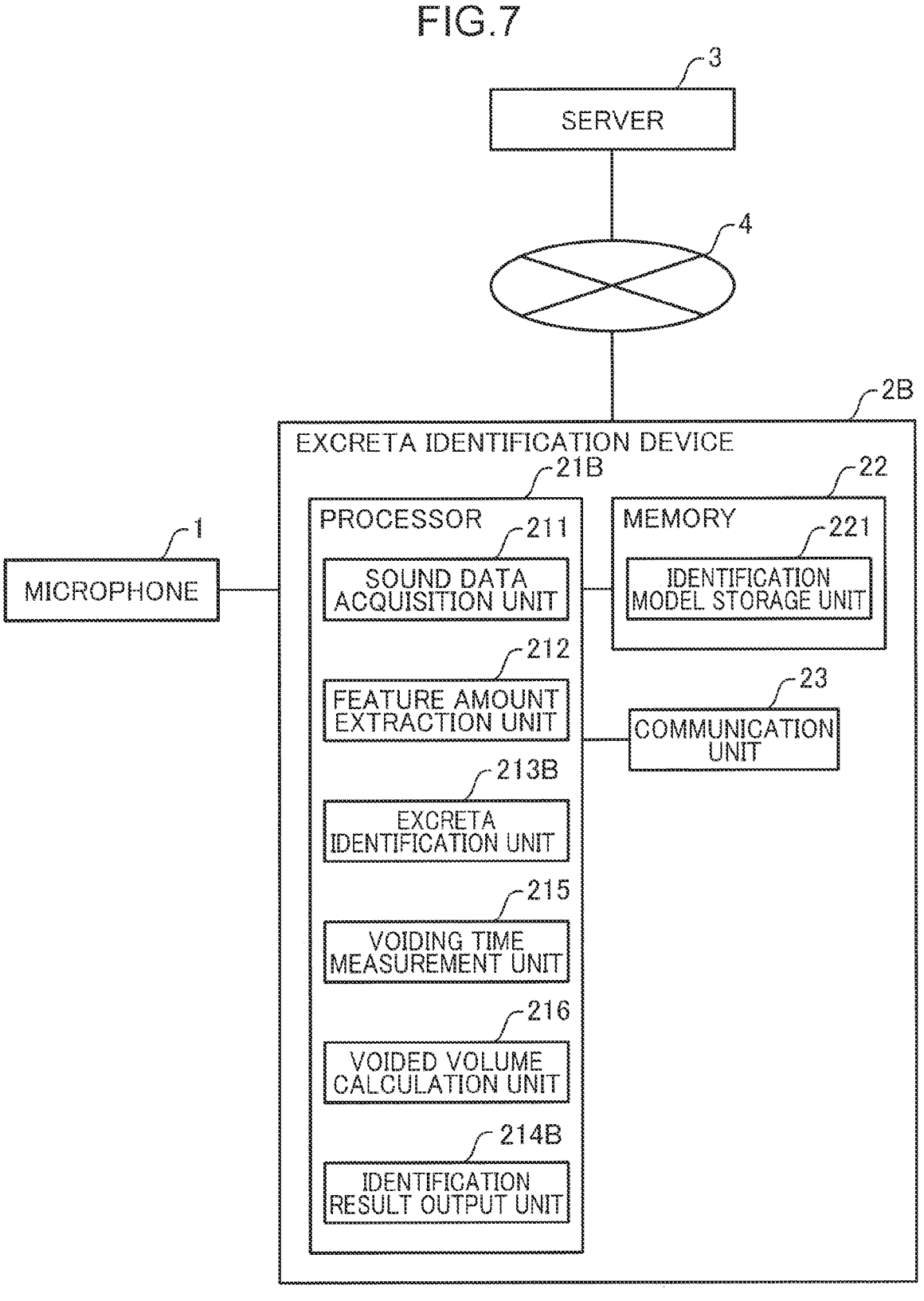
FIG. 7 is a view illustrating a configuration of an excretion management system in a third embodiment of the present disclosure.

FIG. 7 is a view illustrating the configuration of an excretion management system in the third embodiment of the present disclosure. The arrangement positions of the microphone 1 and the excreta identification device 2B in the third embodiment of the present disclosure are the same as the arrangement positions of the microphone 1 and the excreta identification device 2 in the first embodiment.

The excretion management system illustrated in FIG. 7 includes the microphone 1, an excreta identification device 2B, and the server 3. In the present third embodiment, the same components as those in the first embodiment are given the same reference numerals, and description will be omitted.

The excreta identification device 2B includes a processor 21B, the memory 22, and the communication unit 23.

The processor 21B is, for example, a CPU. The processor 21B implements the sound data acquisition unit 211, the feature amount extraction unit 212, an excreta identification unit 213B, a voiding time measurement unit 215, a voided volume calculation unit 216, and an identification result output unit 214B.

The identification model is subjected to machine learning where sound data indicating each of a plurality of levels of urination sound divided according to urine stream is an input value, and which level of urination sound among the plurality of levels of urination sound urination corresponding to has been performed is an output value.

For example, the urination sound is classified, in accordance with to the urine stream, into a first level (weak level) at which the stream is the weakest, a second level (medium level) at which the stream is stronger than that in the first level, and a third level (strong level) at which the stream is stronger than that in the second level. The urination sound of the first level is a sound in which urine drops one by one, the urination sound of the second level is a sound in which urine is continuously excreted, and the urination sound of the third level is a sound in which urine is vigorously excreted.

The urination sound changes in accordance with the urine stream. By specifying the level of the urine stream, it is possible to estimate the amount of urine excreted per predetermined time (for example, one second). Therefore, it is possible to estimate the voided volume using the level of the urine stream and the time of continuous urination.

By inputting the acquired sound data to the identification model, the excreta identification unit 213B identifies as to which level of urination sound among a plurality of levels of urination sound urination corresponding to has been performed.

The voiding time measurement unit 215 measures, as a voiding time, time at which the excreta identification unit 213B has continuously identified that the urination has been performed.

The voided volume calculation unit 216 calculates the voided volume using the level of urination identified by the excreta identification unit 213B and the voiding time measured by the voiding time measurement unit 215. The memory 22 stores a urination level and a unit voided volume excreted per predetermined time (for example, one second) in association with each other. The voided volume calculation unit 216 reads, from the memory 22, the unit voided volume corresponding to the identified level of urination, and multiplies the read unit voided volume by the voiding time, thereby calculating the voided volume.

The identification result output unit 214B outputs an identification result of identifying which of defecation, urination, and flatulating has been performed. When it is identified that urination has been performed, the identification result output unit 214B outputs an identification result indicating that urination has been performed and the voided volume calculated by the voided volume calculation unit 216. When it is identified that urination has been performed, the identification result output unit 214B transmits identification result information indicating that urination has been performed and information indicating a voided volume to the server 3 via the communication unit 23.

When it is identified that any of defecation, urination, and flatulating has been performed, the identification result output unit 214B may transmit, to the server 3 via the communication unit 23, identification result information indicating that any of defecation, urination, and flatulating has been performed and date and time information indicating the date and time when any of defecation, urination, and flatulating is performed. When it is identified that urination has been performed, the identification result output unit 214B may transmit, to the server 3 via the communication unit 23, identification result information indicating that urination has been performed, information indicating the voided volume, and date and time information indicating the date and time when urination is performed.

Next, the excreta identification processing in the excreta identification device 2B according to the third embodiment of the present disclosure will be described.

Figure 8:
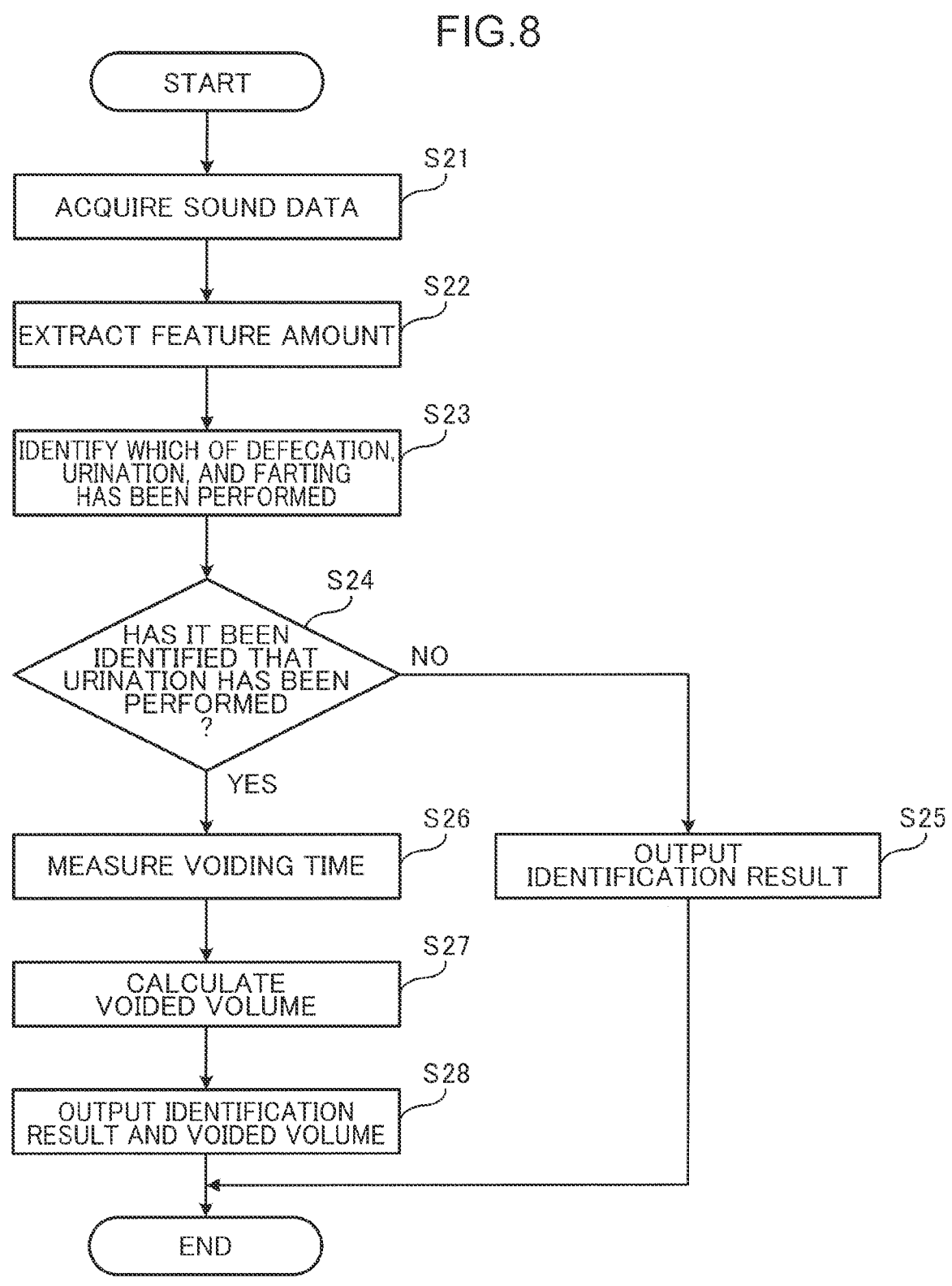
FIG. 8 is a flowchart for describing excreta identification processing in the excreta identification device according to the third embodiment of the present disclosure.

FIG. 8 is a flowchart for describing the excreta identification processing in the exereta identification device 2B according to the third embodiment of the present disclosure.

The processing in steps S21 to S23 is the same as the processing in steps S1 to S3 illustrated in FIG. 3, and thus description is omitted.

Next, in step S24, the voiding time measurement unit 215 determines whether or not the excreta identification unit 213B has identified that urination has been performed. Here, when it is determined that it has not been identified that urination has been performed, that is, when it is determined that defecation or flatulating has been performed (NO in step S24), the identification result output unit 214B outputs in step S25 an identification result as to which of defecation and flatulating has been performed. For example, the identification result output unit 214B transmits, to the server 3 via the communication unit 23, identification result information indicating which of defecation and flatulating has been performed and date and time information indicating the date and time when any of defecation and flatulating was performed.

On the other band, when it is determined that it has been identified that urination has been performed (YES in step S24), the voiding time measurement unit 215 measures in step S26 voiding time of continuous urination.

Next, in step S27, the voided volume calculation unit 216 reads, from the memory 22, the unit voided volume corresponding to the identified level of urination, and multiplies the read unit voided volume by the voiding time, thereby calculating the voided volume.

Next, in step S28, the identification result output unit 214B outputs an identification result indicating that urination has been performed and the voided volume. For example, the identification result output unit 214B transmits, to the server 3 via the communication unit 23, identification result information indicating that urination has been performed, information indicating the voided volume, and date and time information indicating the date and time when urination is performed.

The identification result output unit 214B may store, in the memory 22, identification result information indicating that urination has been performed, information indicating the voided volume, and date and time information indicating the date and time when urination is performed. Furthermore, the memory 22 may include a USB memory connected to a USB port. The identification result output unit 214B may store, in a USB memory, identification result information indicating that urination has been performed, information indicating the voided volume, and date and time information indicating the date and time when urination is performed.

In the present third embodiment, by inputting the acquired sound data to the identification model, the excreta identification unit 213B may identify which of defecation, urination, and flatulating has been performed or the generation situation of environmental sound.

As described above, the urination sound changes in accordance with the urine stream. By identifying the level of the urine stream, it is possible to estimate the amount of urine excreted per predetermined time (for example, one second). Therefore, it is possible to estimate the voided volume using the identified level of urination and the measured time of continued urination.

In each of the above embodiments, each component may be implemented by being configured with dedicated hardware or by executing a software program suitable for each component. Each component may be implemented by a program execution unit such as a CPU or a processor reading and executing a software program recorded in a recording medium such as a hard disk or a semiconductor memory. In addition, the program may be carried out by another independent computer system by recording and transferring the program onto a recording medium or transferring the program via a network.

Some or all of the functions of the devices according to the embodiments of the present disclosure are implemented as large scale integration (LSI), which is typically an integrated circuit. These may be individually integrated into one chip, or may be integrated into one chip so as to include some or all of the functions. Furthermore, the circuit integration is not limited to LSI, and may be implemented by a dedicated circuit or a general-purpose processor. A field programmable gate array (FPGA) that can be programmed after manufacturing of LSI or a reconfigurable processor in which connections and settings of circuit cells inside LSI can be reconfigured may be used.

Some or all of the functions of the devices according to the embodiments of the present disclosure may be implemented by execution of a program by a processor such as a CPU.

In addition, the numbers used above are all illustrated to specifically describe the present disclosure, and the present disclosure is not limited to the illustrated numbers.

In addition, the order in which each step illustrated in the above flowcharts is executed is for specifically describing the present disclosure, and may be an order other than the above order as long as a similar effect is obtained. In addition, some of the above steps may be executed simultaneously (concurrently) with other steps.

INDUSTRIAL APPLICABILITY

Since the technique according to the present disclosure is capable of accurately identifying which of defecation, urination, and flatulating the one who excreted has performed, it is useful as a technique for identifying which of defecation, urination, and flatulating has been performed.

The invention claimed is:

1. An excreta identification method performed by a computer, the method comprising:

acquiring sound data collected by a microphone arranged in a toilet;

identifying which of defecation, urination, flatulating, and the generation of an environmental sound in the toilet has occurred from the acquired sound data by inputting as an input value the acquired sound data into an identification model that has been subjected to machine learning, in which sound data including any of a defecation sound, a urination sound, a flatulating sound, and the environmental sound in the toilet is input into the identification model during the machine learning as an input value, and in which an output value of the identification model during the machine learning identifies which of the defecation, the urination, the flatulating, and the generation of the environmental sound in the toilet has occurred; and outputting an identification result as an output value of the identification model, identifying which of the defecation, the urination, the flatulating, and the generation of the environmental sound in the toilet has occurred, wherein the identification model correlates the urination sound with the speed at which the urine is excreted, and classifies input urination sounds into plural sound levels, each sound level corresponding to an excretion speed of a urine stream, wherein the identification model is subjected to machine learning in which each of the plural sound levels of the urination sounds is input as an input value to the identification model during machine learning and each input urination sound level is correlated with a corresponding urination excretion speed, and in which an output value of identification model during machine learning is the excretion speed associated with a corresponding input urination sound level, and in the identifying operation the identification model identifies the sound level of the urination sound in the acquired sound data in the event a urination sound is present in the acquired sound data, the method further comprising:

measuring the duration of continuous urination based on the duration of the urination sound; and calculating a voided volume of urine voided during urination using the identified sound level of urination, the urination excretion speed corresponding to the identified sound level, and the measured duration.

2. The excreta identification method according to claim 1, wherein the identification model correlates the state of feces excreted during the defecation with a defecation sound produced during the defecation, the identification model is subjected to machine learning in which the input value input into the identification model during machine learning is sound data representing the defecation sound that the identification model correlates with the state of feces, and in which the state of feces is an output value, and in the identification operation, the state of feces is identified by inputting the acquired sound data into the identification model.

3. An excreta identification method performed by a computer, the method comprising:

acquiring sound data collected by a microphone arranged in a toilet;

identifying which of defecation, urination, flatulating, and the generation of an environmental sound in the toilet has occurred from the acquired sound data by inputting as an input value the acquired sound data into an identification model that has been subjected to machine learning, in which sound data including any of a defecation sound, a urination sound, a flatulating sound, and the environmental sound in the toilet is input into the identification model during the machine learning as an input value, and in which an output value of the identification model during the machine learning identifies which of the defecation, the urination, the flatulating, and the generation of the environmental sound in the toilet has occurred; and outputting an identification result as an output value of the identification model, identifying which of the defecation, the urination, the flatulating, and the generation of the environmental sound in the toilet has occurred, wherein the identification model is subjected to machine learning in which sound data of the sound of water splashing on the microphone during the urination, the defecation, the flatulating, or the generation of the environmental sound is an input value input into the identification model, and in which the output value represents the state of the water splashing on the microphone, and in the identification operation, the identification model determines that water is splashed on the microphone by inputting the acquired sound data to the identification model.

4. The excreta identification method according to claim 1, wherein the acquiring operation acquires sound data of sounds generated from the time one who excretes feces, urine, or flatulence sits on a toilet seat to the time when the one who excretes ends their sitting on the toilet seat.

5. The excreta identification method according to claim 1, wherein the microphone is arranged inside a toilet bowl.

6. An excreta identification device comprising:

an acquisition unit that acquires sound data collected by a microphone arranged in a toilet;

an identification unit that identifies which of defecation, urination, flatulating, and the generation of an environmental sound in the toilet has occurred from the acquired sound data by inputting as an input value the acquired sound data into an identification model that has been subjected to machine learning in which sound data including any of a defecation sound, a urination sound, a flatulating sound, and the environmental sound in the toilet is input into the identification model during the machine learning as an input value, and in which an output value of the identification model during the machine learning identifies which of the defecation, the urination, the flatulating, and the generation of the environmental sound in the toilet has occurred; and an output unit that outputs an identification result as an output value of the identification model, identifying which of the defecation, the urination, the flatulating, and the generation of the environmental sound in the toilet has occurred, wherein the identification model correlates the urination sound with the speed at which the urine is excreted, and classifies input urination sounds into plural sound levels, each sound level corresponding to an excretion speed of a urine stream, wherein the identification model is subjected to machine learning in which each of the plural sound levels of the urination sounds is input as an input value to the identification model during machine learning and each input urination sound level is correlated with a corresponding urination excretion speed, and in which an output value of identification model during machine learning is the excretion speed associated with a corresponding input urination sound level, and in the identifying operation the identification model identifies the sound level of the urination sound in the acquired sound data in the event a urination sound is present in the acquired sound data, the device further comprising:

a measuring unit that measures the duration of continuous urination based on the duration of the urination sound; and a calculation unit that calculates a voided volume of urine voided during urination using the identified sound level of urination, the urination excretion speed corresponding to the identified sound level, and the measured duration.

7. A non-transitory computer readable recording medium storing an excreta identification program causing a computer to function to:

acquire sound data collected by a microphone arranged in a toilet;

identify which of defecation, urination, flatulating, and the generation of an environmental sound in the toilet has occurred from the acquired sound data by inputting as an input value the acquired sound data into an identification model that has been subjected to machine learning in which sound data including any of a defecation sound, a urination sound, a flatulating sound, and the environmental sound in the toilet is input into the identification model during the machine learning as an input value, and in which an output value of the identification model during the machine learning identifies which of the defecation, the urination, the flatulating, and the generation of the environmental sound in the toilet has occurred; and output an identification result as an output value of the identification model, identifying which of the defecation, the urination, the flatulating, and the generation of the environmental sound in the toilet has occurred, wherein the identification model correlates the urination sound with the speed at which the urine is excreted, and classifies input urination sounds into plural sound levels, each sound level corresponding to an excretion speed of a urine stream, wherein the identification model is subjected to machine learning in which each of the plural sound levels of the urination sounds is input as an input value to the identification model during machine learning and each input urination sound level is correlated with a corresponding urination excretion speed, and in which an output value of identification model during machine learning is the excretion speed associated with a corresponding input urination sound level, and in the identifying operation the identification model identifies the sound level of the urination sound in the acquired sound data in the event a urination sound is present in the acquired sound data, the program further causing the computer to function to:

measure the duration of continuous urination based on the duration of the urination sound; and calculate a voided volume of urine voided during urination using the identified sound level of urination, the urination excretion speed corresponding to the identified sound level, and the measured duration.

\* \* \* \* \*